(12) United States Patent
Hartog (10) Patent No.: US 10,500,179 B2
(45) Date of Patent: Dec. 10, 2019

(54) GLYCINE FOR USE IN TOLERANCE INDUCTION IN ALLERGIC PATIENTS

(71) Applicant: N. V. Nutricia, Zoetermeer (NL)

(72) Inventor: Anita Hartog, Utrecht (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 15/764,031

(22) PCT Filed: Sep. 30, 2016

(86) PCT No.: PCT/NL2016/050672
§ 371 (c)(1),
(2) Date: Mar. 28, 2018

(87) PCT Pub. No.: WO2017/058016
PCT Pub. Date: Apr. 6, 2017

(65) Prior Publication Data
US 2018/0250253 A1   Sep. 6, 2018

(30) Foreign Application Priority Data
Oct. 2, 2015   (WO) ............... PCT/NL2015/050691

(51) Int. Cl.
| | | |
|---|---|---|
| *A23L 33/175* | (2016.01) | |
| *A61P 37/08* | (2006.01) | |
| *A61K 31/198* | (2006.01) | |
| *A23L 33/00* | (2016.01) | |
| *A61K 38/01* | (2006.01) | |
| *A61K 38/05* | (2006.01) | |
| *A61K 38/06* | (2006.01) | |
| *A61K 38/07* | (2006.01) | |
| *A23L 33/12* | (2016.01) | |
| *A61P 37/06* | (2006.01) | |
| *A61K 31/202* | (2006.01) | |
| *A23L 33/135* | (2016.01) | |

(52) U.S. Cl.
CPC ............ *A61K 31/198* (2013.01); *A23L 33/12* (2016.08); *A23L 33/175* (2016.08); *A23L 33/30* (2016.08); *A23L 33/40* (2016.08); *A61K 31/202* (2013.01); *A61K 38/014* (2013.01); *A61K 38/05* (2013.01); *A61K 38/06* (2013.01); *A61K 38/07* (2013.01); *A61P 37/06* (2018.01); *A61P 37/08* (2018.01); *A23L 33/135* (2016.08); *A23V 2002/00* (2013.01); *A23V 2200/304* (2013.01); *A23V 2250/0622* (2013.01); *A23V 2250/55* (2013.01)

(58) Field of Classification Search
CPC .......... A23V 2200/304; A23V 2200/32; A23V 2200/3202; A23V 2200/3204; A23V 2250/0622; A23V 2250/55; A61K 9/0095; A61K 31/198; A61P 1/00; A61P 1/14; A61P 37/08; A23L 2/66; A23L 29/035; A23L 33/17; A23L 33/175; A23L 33/18; A23L 33/19; A23L 33/30; A23L 33/40
See application file for complete search history.

(56) References Cited

U.S. PATENT DOCUMENTS

| | | | | |
|---|---|---|---|---|
| 8,691,213 | B2 * | 4/2014 | Langford | ............... A23D 9/013 424/535 |
| 2002/0106436 | A1 | 8/2002 | Gohman et al. | |
| 2007/0031534 | A1 * | 2/2007 | Tsujimoto | .............. A23K 10/38 426/2 |
| 2008/0032002 | A1 * | 2/2008 | Anthony | ............... A23L 33/175 426/72 |
| 2010/0215631 | A1 * | 8/2010 | Hartog | ................. A61K 31/198 424/94.1 |
| 2014/0314800 | A1 * | 10/2014 | Knippels | ................. A23L 33/18 424/185.1 |

FOREIGN PATENT DOCUMENTS

| | | |
|---|---|---|
| EP | 0855181 A2 | 7/1998 |
| WO | 9625861 A1 | 8/1996 |
| WO | 2008108651 A1 | 9/2008 |

OTHER PUBLICATIONS

Anonymous: "A Guide for Use in the Child Nutrition Programs", Dec. 1, 2001, United States Department of Agriculture—Agriculture Research Service—Miscellaneous Publication, pp. 43-55 XP002478337.

Lunardi et al. "Glycine-rich cell wall proteins act as specific antigen targets in autoimmune and food allergic disorders". International Immunology, vol. 12, No. 5, May 1, 2000, pp. 647-657, XP055260138, DOI 10.1093/intimm/12.5.647.

Arslanoglu et al. "Early dietary intervention with a mixture of prebiotic oligosaccharides reduces the incidence of allergic manifestations and infections during the first two years of life". The Journal of Nutrition, vol. 138, No. 6, Jun. 1, 2008, pp. 1091-1095, XP055031734.

\* cited by examiner

*Primary Examiner* — Jeffrey E. Russel
(74) *Attorney, Agent, or Firm* — Banner & Witcoff, Ltd.

(57) ABSTRACT

The invention relates to a free glycine source for use in inducing tolerance against an allergen, or preventing the development of allergy in a human or other mammal. The invention further relates to a composition comprising protein, fat and carbohydrates with at least 7 en % protein and at least 60 mg free glycine source per gram protein, preferably at least 70 mg glycine per gram protein. The free glycine source is preferably the free amino acid glycine, a salt of the free amino acid glycine, or a combination thereof; the protein can be intact protein, hydrolysed protein, peptides, free amino acids, salts of amino acids, or combinations thereof.

18 Claims, 4 Drawing Sheets

GLYCINE FOR USE IN TOLERANCE INDUCTION IN ALLERGIC PATIENTS

RELATED APPLICATION DATA

This application is a National Stage Application under 35 U.S.C. 371 of co-pending PCT application PCT/NL2016/050672 and filed on Sep. 30, 2016; which claims priority to PCT application PCT/NL2015/050691 and filed on Oct. 2, 2015.

BACKGROUND OF THE INVENTION

The invention relates to a composition comprising at least one free glycine source selected from the group of the free amino acid glycine, physiologically acceptable salts of the free amino acid glycine, dipeptides having at least one glycine unit, tripeptides having at least one glycine unit and tetrapeptides having at least one glycine unit for use in preventing an allergy in a human or other mammal.

Allergy is a burdensome disease that is increasingly present in the world. Allergy against allergens can develop from day 1 after birth until adult age. In particular food allergy starts early in life when the infant is exposed to new food allergens. The atopic march is still believed to start with food allergy where later in life airway allergens become relevant inducing allergic rhinitis and asthma.

The typical treatment strategy for (food)-allergy is avoidance of the allergen. Avoidance will dissolve the allergen induced symptoms without inducing tolerance.

The induction of tolerance against food proteins is a naturally occurring non-pathogenic immune-response that, when not induced, can give rise to allergies. Although many processes involved in the induction of tolerance are discovered, it is still unknown why immunological tolerance is not always induced.

EP 0855 181 A2 relates to the use of glycine, L-alanine and/or L-serine, in free amino acid form and/or in physiologically acceptable salt form in the preparation of a medicament or nutritional formulation with immune-modulating effect. Also treatment of allergic inflammatory reactions is described, i.e. treatment of manifest symptoms of an allergy in an allergic patient. The prevention of an allergy is not described in this document, and in particular it is not disclosed or suggested to use glycine to induce immunological tolerance to the allergens. The inhibition of inflammation is clearly different from the presently claimed prevention of allergy or induction of immunological tolerance because the induction of tolerance (the prevention of allergy) makes the use of anti-inflammatory agents unnecessary. The presently claimed solution to the problem of immunological tolerance induction would thus prevent the need to look for anti-inflammatory agents.

EP 2 061 346 A1 discloses the use of a nutritional composition comprising at least 99 wt % free amino acids based on total protein of the composition for decreasing sensitivity of a subject to an allergen. That is, in EP 2 061 346 the symptoms of allergy and infections are decreased by decreasing sensitivity to said allergen, even though the underlying allergy remains. EP 2 061 346 provides an allergic person with a nutritional composition free of potential allergens. The presently claimed composition has been found to actually prevent allergy, i.e. inducing or improving immunological tolerance against an allergen.

US 2002/106436 A1 similarly relates to an infant formula powder for infants with milk allergy, comprising free amino acids as protein source to prevent allergic reactions against milk protein. Glutamine is present in 2-3 g/1000 kcal of the composition supposedly beneficial for healing to the infant's damaged gut and normal growth. There is no mentioning of tolerance induction to (milk) proteins in this document, nor of the prevention of the allergy itself.

There remains a need for compositions useful to actually reduce the risk of a human or other mammal to develop an allergy, such as by inducing or improving an immunological tolerance against allergens in allergic subjects.

SUMMARY OF THE INVENTION

The inventors surprisingly found that the amino acid glycine, in particular free glycine, supports the development of immunological tolerance to an allergen. This was the first time to show this tolerogenic effect of glycine. The inventors concluded that hereby glycine is useful in preventing an allergy. The found effect of glycine (provided as free amino acid, salt thereof, or as a small peptide) on improving immunological tolerance is distinct from anti-inflammatory effects of glycine. This effect is also distinct from effects of known medicaments, such as corticosteroids used for suppressing the inflammatory response during an allergic reaction.

The invention therefore relates to a free glycine source for use in inducing or improving tolerance against an allergen or preventing the development of an allergy in a human or other mammal, in particular in a patient suffering from an allergy. Said free glycine source is selected from the group of the free amino acid glycine, physiologically acceptable salts of the free amino acid glycine, dipeptides having at least one glycine unit, tripeptides having at least one glycine unit and tetrapeptides having at least one glycine unit. Said free glycine source is preferably the free amino acid glycine, a salt of the free amino acid glycine, or a combination thereof.

The invention further relates to a composition comprising protein, fat and carbohydrate, having at least 7 en % protein and at least 60 mg, preferably at least 70 mg, of a free glycine source per gram protein and the protein consist of at least 80 wt % intact or hydrolysed protein based on total weight of the protein in the composition. The protein can be intact protein, hydrolysed protein, peptides, free amino acids, salts of amino acids, or a combination thereof.

BRIEF DESCRIPTION OF THE DRAWINGS

FIGS. 2A-2C depict the results of glycine intake before sensitization inhibitions.

DETAILED DESCRIPTION OF THE INVENTION

Prevention of an Allergy & Tolerance Induction

In accordance with the invention, preventing the development of allergy means that a human or mammal is prevented from developing hypersensitivity of the immune system to an allergen, i.e. tolerance against an allergen is induced or improved, and/or allergy development is inhibited. In particular, the prevention of an allergy is the prevention of developing hypersensitivity of the immune system to an allergen present in food, in particular a food protein, more in particular a milk protein.

The free glycine source for use in preventing the allergy is in particular effective by inducing or improving immunological tolerance against an allergen.

The term 'immunological tolerance' (or in short 'tolerance') is generally known in the art. It is a state of specific immunological unresponsiveness to an allergen. Both humoral and cell-mediated pathways of the immune response may be suppressed by tolerance induction.

Tolerance induction against food allergens occurs naturally after birth, or maybe even before birth, where the immune system of the infant learns how to react against new antigenic epitopes. In a significant amount of infants, children and adults, the immune system makes a mistake and reacts against epitopes by producing large amounts of Immunoglobulin E (IgE). This IgE can bind the epitopes using its antigen binding side and at the same time can also bind to IgE receptors that are present on a large number of immune cells. These events will lead to a cascade of reactions regulated by complex mechanisms, leading to a whole range of allergic symptoms in the skin, upper respiratory tract, or mucus layers anywhere in the body (lung, eyes, intestines, etc). Antigen specific IgE is seen as a major indicator for food allergy.

The cells that produce IgE are called B-cells and are regulated by a number of different cells such as T-cells, dendritic cells, etc. If anywhere in the complex regulatory system there is a 'failure', allergy can occur.

The term "Tolerance" for the purpose of this invention means that, in the non-allergic human or other mammal, will be essentially non-responsive against allergens leading to an allergic reaction, i.e. an allergic reaction is avoided. In particular, an improved tolerance may include a decrease in the production antigen specific IgE (up to a total avoidance). In particular, the determination of the absence or decrease of allergen specific IgE and skin prick tests are often used as marker for allergy and tolerance induction in IgE mediated allergies.

As illustrated by Example 2, in practice, the effectivity of a composition (for use) according to the invention in preventing a (specific) allergy can be determined by comparing a test group of subjects not allergic to a (specific) allergen that are treated with the glycine source (TG) with a control group (likewise not allergic to the (specific) allergen) not treated with glycine (CG) but with a placebo. After (start of) the treatment with the glycine source respectively the placebo, both groups are subjected to a sensitizing treatment with the allergen. If the incidence of subjects developing a hypersensitivity of the immune system to the allergen is less in TG than in CG, the treatment is effective in prevention of the allergy.

However, the most accurate test for testing food allergy or tolerance induction is the double blind—placebo controlled oral food challenge (DBPCFC; see J Allergy Clin Immunol. 1988 December; 82(6):986-97. Double-blind, placebo-controlled food challenge (DBPCFC) as an office procedure: a manual Bock SA1, Sampson H A, Atkins F M, Zeiger R S, Lehrer S, Sachs M, Bush R K, Metcalfe D D).

Without being bound by theory, the inventors realized that the compositions according to the invention support tolerance induction in order to prevent non-IgE mediated allergy. As illustrated in the Examples, a free glycine source has also been found to have an inhibiting effect on crosslinking induced TNF-alpha, IL-4 and IL-13 production, which supports that free glycine inhibits allergy development. Further it is shown in the Examples that a free glycine source has a positive effect on mMCP-1 release. More mentioned readouts (cytokines and mast cell protease) are known to be involved in induction, maintenance and enhancement of an allergic reaction. Inhibiting the production of these readouts is an indication for preventing an allergic response and supports tolerance induction as indicated by this invention.

Protein

The term "protein" is defined as any compound composed of one or more amino acids; the term in particular includes free amino acids, salts thereof, peptides, hydrolysed protein and intact protein.

The present invention advantageously concerns the use of a composition wherein the protein source provides 7 to 20% of the total calories of the composition, preferably the protein source provides 8 to 17% of the total calories, even more preferably the protein source provides 9 to 15% of the total calories of the composition.

For determining the percentage of total calories (en %) of the composition (for use) according to the invention, the contribution of proteins is 4 kcal/g, the contribution of fats is 9 kcal/g and the contribution of digestible carbohydrates is 4 kcal/gram.

Allergy patients normally have an overreacting immune response against specific protein allergens. In particular food allergy is caused by many food related proteins. Cow's milk proteins are the most common allergens in infancy, followed by chicken egg proteins. Other common forms of food allergy are legume allergies (e.g. peanut allergy, soy protein allergy), allergies to nuts and allergies to seafood.

In a preferred composition for use according to the present invention, the protein source consists of free amino acid(s) and/or salt(s) thereof, and the protein source provides—in total—between 10 and 20 wt % free amino acid(s) and/or salt(s) thereof based on dry weight of the total composition, preferably between 11 and 18 wt %, and even more preferably between 12 and 16 wt % free amino acid(s) and/or salt(s) thereof based on dry weight of the total composition.

In a further preferred composition for use according to the present invention, the protein source consists of free amino acid(s) and/or salt(s) thereof plus one or more peptides having up to 7 amino acid units, in particular one or more peptides selected from the group of dipeptides, tripeptides and tetrapeptides, and the protein source provides—in total—between 10 and 20 wt % free amino acid(s) and/or salt(s) thereof based on dry weight of the total composition, preferably between 11 and 18 wt %, and even more preferably between 12 and 16 wt % free amino acid(s) and/or salt(s) thereof based on dry weight of the total composition.

In a further preferred composition the comprises one or more intact proteins with added free glycine source.

In a specific embodiment, the composition for the use according to the present invention is an infant formula wherein the protein source comprises all essential amino acids (phenylalanine, valine, threonine, tryptophan, methionine, leucine, isoleucine, lysine, and histidine). A suitable amino acid profile for an infant formula is known in the art. A preferred embodiment of an amino acid composition of a composition according to the invention is given in Table 1.

Glycine

The protein source of the composition according to the invention should comprise a free glycine source. The free glycine source is typically formed of at least one component selected from the group of free glycine ($NH_2CH_2COOH$), salts of glycine, dipeptides having one or two glycine units, tripeptides having one, two or three glycine units and tetrapeptides having one, two, three or four glycine units. Glycine as present in proteins or larger peptides of more than 4 amino acids is not sufficiently rapidly taken up into the mucosal tissue or blood and can therefore not reach effective levels in blood. To have an effective amount of glycine the protein source has a free glycine source content of at least 6% glycine, preferably at least 7% glycine, more preferably at least 10% glycine even more preferably at least 15% glycine and most preferably at least 20% glycine based on total amino acids in the composition.

Collagen hydrolysate, is a good source of free glycine for applications wherein collagen hydrolysate is acceptable. For infant formulae collagen hydrolysate is generally not used, but it can be used for compositions intended for adolescents and adults. Such collagen hydrolysate preferably has an number average peptide size of 4 or less amino acids. In a preferred nutritional composition, the amount of protein is preferably in the range of 7-20 en % and the amount of free glycine source in a range of 60-350 mg/g protein, preferably 70-350 mg/g protein, more preferably 80-325 mg/g protein even more preferably 90-300 mg/g protein mg/g protein. If glycine is present as a salt the amount of glycine provided by the salt can be calculated using the formula: Gram glycine=Mole glycine salt×Molar mass of glycine. The amount of other free amino acids e.g. glutamine can be calculated analogously.

If free glycine source is present as a derivative, such as an oligopeptide (having up to four amino acid units) having one or more glycine units, the amount of glycine provided by the derivative can be calculated using the formula: Gram glycine=Mole glycine derivative×Molar mass of glycine. The amount of other amino acid derivatives e.g. glutamine derivatives can be calculated analogously.

Glutamine

The composition for use according to the invention preferably comprises a free glutamine source in addition to the free glycine source. Preferably the glutamine source is selected from the group of free glutamine and salts thereof, including combinations thereof. A derivative, typically an oligopeptide, analogously to the above mentioned glycine derivatives may also be used. If free glutamine is present, the molar ratio free glycine:free glutamine usually is at least 1:4, in particular at least 1:2.5 for an advantageous effect. Usually said ration is 1:2 or less. Preferably the ratio free glycine:free glutamine of the product is between 1:4 and 1:1.

Carbohydrate

The composition according to the invention may comprise a carbohydrate fraction, which may include a prebiotic. In the context of the present invention, the term "prebiotic" refers to one or more non-digestible oligosaccharides. Advantageously, the non-digestible oligosaccharide is water-soluble. Non-digestible oligosaccharides are not digested in the intestine by the action of digestive enzymes present in the human upper digestive tract (small intestine and stomach) but instead are fermented by the human intestinal microbiota. Suitable non-digestible oligosaccharides are selected from the group consisting of fructo-oligosaccharide, non-digestible dextrin, galacto-oligosaccharide, xylo-oligosaccharide, arabino-oligosaccharide, arabinogalactooligosaccharide, gluco-oligosaccharide, glucomannooligosaccharide, galactomanno-oligosaccharide, mannanoligosaccharide, chito-oligosaccharide, uronic acid oligosaccharide, sialyl-oligosaccharide and fuco-oligosaccharide. Especially suitable non-digestible oligosaccharides are fructo-oligosaccharides and/or galacto-oligosaccharides. The oligosaccharides suitably have a degree of polymerization of 2-200. In one embodiment, fructo-oligosaccharides and fructo-polysaccharides (and mixtures thereof) with a DP of 2-200 are suitable prebiotics in the context of the invention. One suitable type of oligosaccharide is a short-chain oligosaccharide which has an average degree of polymerisation of less than 10, suitably at most 8, suitably in the range of 2-7. The short-chain oligosaccharide suitably comprises galacto-oligosaccharides and/or fructo-oligosaccharides. In one embodiment, the composition comprises galacto-oligosaccharides, in particular beta-galacto-oligosaccharides, more in particular trans-galacto-oligosaccharides. The galacto-oligosaccharides suitably have an average degree of polymerisation in the range of 2-8, i.e. are short-chain oligosaccharides in the context of the invention.

Suitably, the composition comprises short-chain fructo-oligosaccharides and/or short-chain galacto-oligosaccharides, suitably at least short-chain fructo-oligosaccharides. (trans)galactooligosaccharide is for example available under the trade name Vivinal® GOS (Borculo Domo Ingredients, Zwolle, Netherlands), Bimuno (Clasado), Cup-oligo (Nissin Sugar) and Oligomate55 (Yakult). Fructooligosaccharides may be inulin hydrolysate products having an average DP within the aforementioned (sub-) ranges; such FOS products are for instance commercially available as Raftilose P95 (Orafti) or with Cosucra.

Another suitable type of oligosaccharide is long-chain fructo-oligosaccharides which has an average degree of polymerisation above 10, typically in the range of 10-100, suitably 15-50, most suitably above 20. A particular type of long-chain fructo-oligosaccharides is inulin, such as Raftilin HP.

The present composition may contain one type of non-digestible oligosaccharide or a mixture of two or more types of non-digestible oligosaccharides, suitably it comprises a mixture of two or more non-digestible oligosaccharides, most suitably a mixture of two non-digestible oligosaccharides. In case the prebiotic contains or consists of a mixture of two distinct oligosaccharides, one oligosaccharide may be short-chain as defined above and one oligosaccharide may be long-chain as defined above. Suitably, short-chain oligosaccharides and long-chain oligosaccharides are present in a weight ratio short-chain to long-chain in the range of 1:99-99:1, more suitably 1:1-99:1, more suitably 4:1-97:3, even more suitably 5:1-95:5, even more suitably 7:1-95:5, even more suitably 8:1-10:1, most suitably about 9:1.

In one embodiment, the prebiotic comprises a mixture of fructo-oligosaccharides and/or galacto-oligosaccharides. Suitable mixtures include mixtures of long-chain fructo-oligosaccharides with short-chain fructo-oligosaccharides or short-chain galacto oligosaccharides, most suitably long-chain fructo-oligosaccharides with short-chain fructo-oligosaccharides. In one embodiment, the prebiotic comprises a mixture of fructo-oligosaccharides, most 5 suitably a mixture of short-chain fructo-oligosaccharides (sc-FOS) and long-chain fructo-oligosaccharides (lc-FOS). These fructo-oligosaccharides suitably account for at least 80 wt %, more suitably at least 90 wt % of the prebiotic. In a most suitable embodiment, the prebiotic fraction consists of a mixture of sc- and lc-FOS.

The prebiotics may be present in the composition at any suitable concentration. In an embodiment, the present composition comprises 0.05 to 20 wt % of said non-digestible oligosaccharides, more suitably 0.5 to 15 wt %, even more suitably 1 to 10 wt %, most suitably 2 to 10 wt %, based on dry weight of the present composition. When in liquid form, the present composition suitably comprises 0.01 to 2.5 wt % non-digestible oligosaccharide, more suitably 0.05 to 1.5 wt %, even more suitably 0.25 to 1.5 wt %, based on 100 ml.

The composition according to the invention may comprise further carbohydrates, suitably the present composition comprises a digestible carbohydrate. Typically, digestible carbohydrates that are known in the art to be suitable for use in infant nutritional compositions are used. Suitably, the digestible carbohydrate is selected from digestible polysaccharides (e.g. starch, matodextrin), digestible monosaccharides (e.g. glucose, fructose), and digestible disaccharides (e.g. lactose, sucrose). Particularly suitable is lactose and/or maltodextrin. In one embodiment, the composition does not comprise lactose.

The digestible carbohydrate component may comprise lactose. In an embodiment, the composition suitably comprises at least 60 wt % lactose based on total digestible carbohydrate, more suitably at least 75 wt %, even more suitably at least 90 wt % lactose based on total digestible carbohydrate.

Lipid

In an embodiment, the composition according to the invention comprises a lipid component. Suitable lipid components, e.g. suitable for infant nutrition, are known in the art. In an embodiment, the lipid component of the present composition suitably provides 2.9 to 6.0 g, more suitably 4 to 6 g per 100 kcal of the composition. When in liquid form, the composition comprising a lipid component suitably comprises 2.1 to 6.5 g lipid per 100 ml, more suitably 3.0 to 4.0 g per 100 ml. Based on dry weight the present infant or follow on formula suitably comprises 12.5 to 40 wt % lipid, more suitably 19 to 30 wt %.

The lipid component preferably comprises one or more long chain polyunsaturated fatty acids (LC-PUFA). The LC-PUFA usually have a chain length of 18-24 carbon atoms, The LC-PUFAs may be provided as free fatty acids, in triglyceride form, in diglyceride form, in monoglyceride form, in phospholipid form, or as a mixture of one of more of the above. Further preferred LC-PUFA's are arachidonic acid (ARA), docosahexaenoic acid (DHA) and eicosapentaenoic acid (EPA). The concentration LC-PUFA is preferably between 0.05 and 0.5 wt % based on the total lipid content. Advantageously the essential fatty acids alphalinolenic acid (ALA) and/or linoleic acid (LA) are present in a composition according to the invention these fatty acids are precursors of LC-PUFA production in the body.

Suitably the present composition contains at least one, suitably at least two lipid sources selected from the group consisting of rape seed oil (such as colza oil, low erucic acid rape seed oil and canola oil), high oleic sunflower oil, high oleic safflower oil, olive oil, marine oils, microbial oils, coconut oil, palm kernel oil and milk fat.

Probiotic

In an embodiment, the composition according to the invention comprises a probiotic. In the context of the present invention, the term "probiotic" refers to a strain of probiotic bacteria. Probiotic bacteria are known in the art. Suitably, the probiotic bacteria are not genetically modified.

Suitable probiotic bacteria include bacteria of the genus Bifidobacteria (e.g. B. breve, B. longum, B. infantis, B. bifidum), Lactobacillus (e.g. L. Acidophilus, L. paracasei, L. johnsonii, L. plantarum, L. reuteri, L. rhamnosus, L. casei, L. lactis), and Streptococcus (e.g. S. thermophilus). B. breve and B. longum are especially suitable probiotics.

Most suitably, the probiotic comprises a strain of B. breve. The B. breve suitably has at least 95% identity of the 16 S rRNA sequence when compared to the type strain of B. breve ATCC 15700, more suitably at least 97% identity (Stackebrandt & Goebel, 1994, Int. J. Syst. Bacteriol. 44:846-849). Suitable B. breve strains may be isolated from the faeces of healthy human milk-fed infants. Typically, these are commercially available from producers of lactic acid bacteria, but they can also be directly isolated from faeces, identified, characterised and produced. According to one embodiment, the present composition contains a B. breve selected from the group consisting of B. breve Bb-03 (Rhodia/Danisco), B. breve M-16V (Morinaga), B. breve R0070 (Institute Rosell, Lallemand), B. breve BR03 (Probiotical), B. breve BR92) (Cell Biotech), DSM 5 20091, LMG 11613, YIT4065, FERM BP-6223 and CNCM 1-2219. Most suitably, the B. breve is selected from the group consisting of B. breve M-16V and B. breve CNCM 1-2219, most suitably B. breve M-16V. B. breve 1-2219 was published in WO2004/093899 and was deposited at the Collection Nationale de Cultures de Microorganisms, Institute Pasteur, Paris, France on 31 May 1999 by Compagnie Gervais Danone. B. breve M-16V was deposited as BCCM/LMG23729 and is commercially available from Morinaga Milk Industry Co., Ltd.

The combination of a prebiotic and a probiotic is also referred to as a "synbiotic". The probiotic may be present in the composition at any suitable concentration, suitably in a therapeutically effective amount or "amount effective for treating" in the context of the invention. Suitably, the probiotic is included in the present composition in an amount of $10^2$-$10^{13}$ cfu per g dry weight of the composition, suitably $10^5$-$10^{12}$ cfu/g, most suitably $10^7$-$10^{10}$ cfu/g.

Application

The composition according to the invention is generally used for preventing an allergy, in particular for supporting the induction of immunological tolerance in a subject by inhibiting allergy development. The allergy may be food allergy. Such prevention of allergy generally involves avoiding the (acute) symptoms associated with ingesting an allergen, in particular wherein the allergen is cow's milk protein. Suitably, the (acute) symptoms are avoided when the allergen is ingested again, e.g. in a double blind, placebo controlled oral provocation test (DBPC-test) or with a skin prick test.

The invention is in particular useful for administration to a human or other mammal having a relatively large risk of developing a (specific) allergy. Such humans and other mammals include humans and other mammals having a genetic predisposition. In particular, humans and other mammals of which at least one parent has an atopic disorder and/or an allergy, such as a food allergy, are advantageously treated with a composition according to the invention in order to prevent an allergy, such as a food allergy.

The composition according to the invention can be used as a nutritional composition, nutritional therapy, nutritional support, as a medical food, as a food for special medical purposes or as a nutritional supplement. The present composition is suitably an enteral composition. The composition is administered to, or intended to be administered to, a subject in need thereof, in particular to a subject selected from the group consisting of children and infants, including toddlers, suitably children up to 6 years of age, suitably infants typically with an age of 0-36 month, more suitably 0-12 months of age, most suitably 0-6 months of age. Thus, in some embodiments, the present composition is an infant formula, follow-on formula or growing-up milk; most suitably it is an infant formula.

In a particular embodiment, the composition is for administration to subjects, in particular infants, at risk of developing allergy, especially cow's milk protein allergy (CMA). Infants that are known to be at risk of developing allergy include infants born from at least one parent who suffers from, or has suffered from, an atopic disorder (e.g. eczema) and/or an allergy, most in particular from CMA.

The present composition is suitably administered in a daily dose providing at least 0.01 mg glycine (provided by the free glycine source) per kg body weight of the subject that is treated. The daily dosage per kg body weight of the subject is usually 2 g glycine (provided by the free glycine source) or less. Preferably the daily dosage per kg body weight is 0.1-2 g glycine (provided by the free glycine source), more preferably 0.1-1 g glycine, more suitably 0.1-100 mg, more specifically 0.5-5 mg, most specifically 1-2.5 mg per kg body weight.

In a further aspect, the present invention further relates to a kit-of-parts comprising or consisting of the following two or three different containers and instructions for use: A first container comprising infant nutrition, a second container comprising a free glycine source and optionally a third container comprising a probiotic or synbiotic as defined hereinabove. Alternatively, the probiotic or synbiotic can be comprised in the first container.

The infant nutrition is suitably an infant formula, follow-on formula or growing-up milk as known in the art. Most suitably, the infant nutrition is specifically targeted for infants at risk of developing allergy, in particular wherein the allergy is CMA. Formulae for infant nutrition are known in the art. The infant nutrition may also be referred to as the composition according to the invention as defined hereinabove.

The infant nutrition may or may not comprise the probiotic as defined above. In case the infant nutrition does not contain the probiotic, the kit of parts preferably comprises a third container comprising the probiotic. The third container is typically in the form of a sachet or stickpack and suitably comprises a powder essentially consisting of the probiotic and a acceptable carrier, typically lactose. The second container is typically in sachet or stickpack and suitably comprises a powder essentially consisting of glycine and optionally an acceptable carrier, typically maltodextrin. The instructions for use conveniently instruct the user to combine the contents of the two or three containers in the appropriate format and reconstitute the resulting mixture with a liquid, typically water, to obtain a ready-to-use liquid composition.

The invention furthermore provides a method for inducing or improving tolerance against an allergy or for preventing an allergy, comprising administering to a human or other mammal, a composition comprising at least one free glycine source selected from the group of the free amino acid glycine, physiologically acceptable salts of the free amino acid glycine, dipeptides having at least one glycine unit, tripeptides having at least one glycine unit and tetrapeptides having at least one glycine unit, the composition comprising at least 7 en % protein ('protein' being defined as compounds composed of one or more amino acids, the term including free amino acids, salts thereof, hydrolysed proteins and intact protein) and the total content of glycine provided by the free glycine source being 60-350 mg/g protein.

EXAMPLES

TABLE 1

Preferred amino acid composition according to the invention

| Amino Acids | Preferred mg/g amino acids | Particularly preferred mg/g amino acids |
|---|---|---|
| Alanine | 36-40 | 38.7 |
| Arginine | 62-67 | 64.5 |
| Aspartic acid | 62-67 | 64.5 |
| Cysteine | 24-28 | 26.0 |
| Glutamine | 81-87 | 83.8 |
| Glycine | 78-84 | 80.6 |
| Histidine | 36-40 | 38.7 |
| Iso-leucine | 61-66 | 63.5 |
| Leucine | 100-110 | 105 |
| Lysine | 68-74 | 71.0 |
| Methionine | 15-18 | 16.8 |
| Phenylalanine | 43-48 | 45.5 |
| Proline | 71-77 | 74.4 |
| Serine | 43-48 | 45.5 |
| Threonine | 48-54 | 51.5 |
| Tryptophan | 18-22 | 20.6 |
| Tyrosine | 44-49 | 46.5 |
| Valine | 62-67 | 64.5 |

Example 1. Glycine Attenuates Cytokine Production in a Rat Basophil Leukemia In Vitro Model Basophilic granulocytes play an important role in the allergic reaction. In vivo this cell type produces histamine and leukotriene's and several inflammatory cytokines upon stimulation by antigens that are seen as important mediators causing allergic symptoms in humans.

RBL-2H3 cells were sensitized by 100 ng/ml mouse IgE α-dinitrophenyl in culture medium (DMEM with 10% FBS and 1% penicillin/streptavidin) and plate out 100 µl/well in a 96-well flat bottom plate. After 18 hrs of culturing at 37° C. with 5% CO2, the cells were washed 4 times with 200 µl Tyrode's buffer (130 mM NaCl, 190 mM KCl, 1.4 mM $CaCl_2$, 1 mM $MgCl_2$, 5.6 mM glucose, 10 mM HEPES, and 0.1% bovine serum albumin in distilled water, pH 7.4). 25 µl glycine in a concentration series starting form 500 µg/ml and diluted 1:1 in Tyrode's buffer (component), 25 µl Tyrode's buffer (controls) or 25 µl quercetin 100 µM (positive control) were added to the cells. 25 µl of DNP-BSA (100 ng/ml) and 50 µl Tyrode's buffer were added to each component well.

After 20 hours incubation at 37° C. with 5% $CO_2$ 90 µl of the cells supernatant was collected and stored at −80° C. for cytokine analysis by multiplex bead immunoassay.

The remaining RBL-2H3 cells were used for a WST assay to measure the influence of the glycine on the metabolic activity of the cells.

Results

Figure 1A:
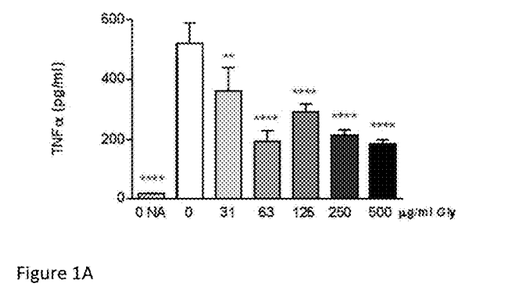
FIGS. 1A-1C depict the results of glycine inhibition of the crosslinking induced TNFα (FIG. 1A), IL-4 (FIG. 1B) and IL-13 (FIG. 1C) production in a concentration dependent way.
Figure 1B:
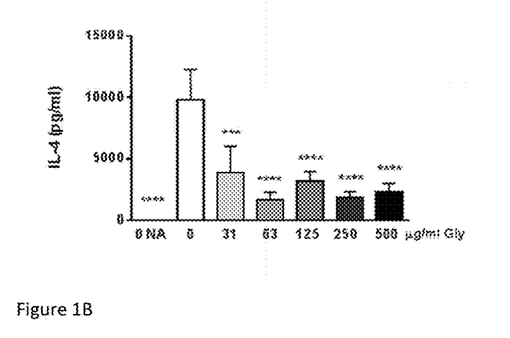
Figure 1C:
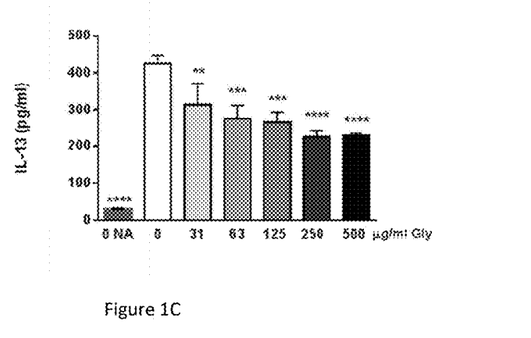

Glycine inhibits the crosslinking induced TNFα, IL-4 and IL-13 production in a concentration dependent way, as illustrated by FIGS. 1A-1C. This inhibition of IL-4 and IL-13 is of particular relevance, since both cytokines are pivotal in the reactive allergic cascade. IL-4 and IL-13 can be secreted by CD4+ Th2 cells, activated basophils and mast cells. They direct/induce Th2 cell differentiation, B cell Ig class switch to IgE and initiate mast cell mediated mucosal barrier disruption. Although there is functional overlap between these cytokines, there is substantial evidence that IL-13 functions as a primary disease-inducing effector cytokine, whereas IL-4 acts as a key amplifier of type 2 immunity by facilitating the expansion of Th2 cell populations in the secondary lymphoid organs, but also by inducing mast cell amplification in food allergy. Therefore, the glycine-induced inhibition of IL-4 and IL-13 production by basophils, as shown in the present study with RBL cells, might be followed by a reduced Th2 cell activation and improved intestinal integrity resulting in a decreased allergy development.

Example 2. Glycine Induces Tolerance in Mouse Model

Infants can become allergic to allergens through mothers milk or other oral challenges. To investigate if it is possible to induce tolerance induction instead of inducing allergy, the inventors used a mouse model where glycine is given before and during the sensitization phase. IgE production is generally accepted as a marker for allergy induction (both in humans and in the present mouse model). Ear swelling is a marker of T-cell infiltration and is generally accepted as marker for allergy in this mouse model. The larger the ear swelling after challenge the stronger the allergic response. Similar to basophil stimulation of Example 1, mast cells produce mediators like histamine, pro-inflammatory cytokines. In mice, mast cell protease-1 is a marker used to measure the release of these mediators from mast cells upon oral allergic stimulation.

In the present model, mice were sensitized against bovine whey protein according to standard protocol. In short: Female C3H/HeOuJ mice were supplemented with or without Gly by oral gavage (50 or 100 mg/mouse) 24 and 4 hours before sensitization (weekly for 5 times) with the cow's milk protein whey (20 mg), using cholera toxin (10 µg) as adjuvant. The negative control group only received diluent (without glycine) and cholera toxin (without whey).

Acute allergic skin responses were assessed after intradermal allergen challenge in the ear (10 µl of 1 mg whey/ml). Serum for mouse mast cell protease-1 (mMCP-1) and whey specific IgE levels were collected one hour after an oral allergen challenge (50 mg whey) and assessed by ELISA according to standard protocol of the supplier.

Groups
A. Negative control (diluent 24 hr and 4 hr before cholera toxin)
B. Positive control (diluent 24 hr and 4 hr before whey+cholera toxin)
C. 50 mg glycine (50 mg glycine 24 hr and 4 hr before whey+cholera toxin)
D. 100 mg glycine (100 mg glycine 24 hr and 4 hr before whey+cholera toxin)

Figure 2A:
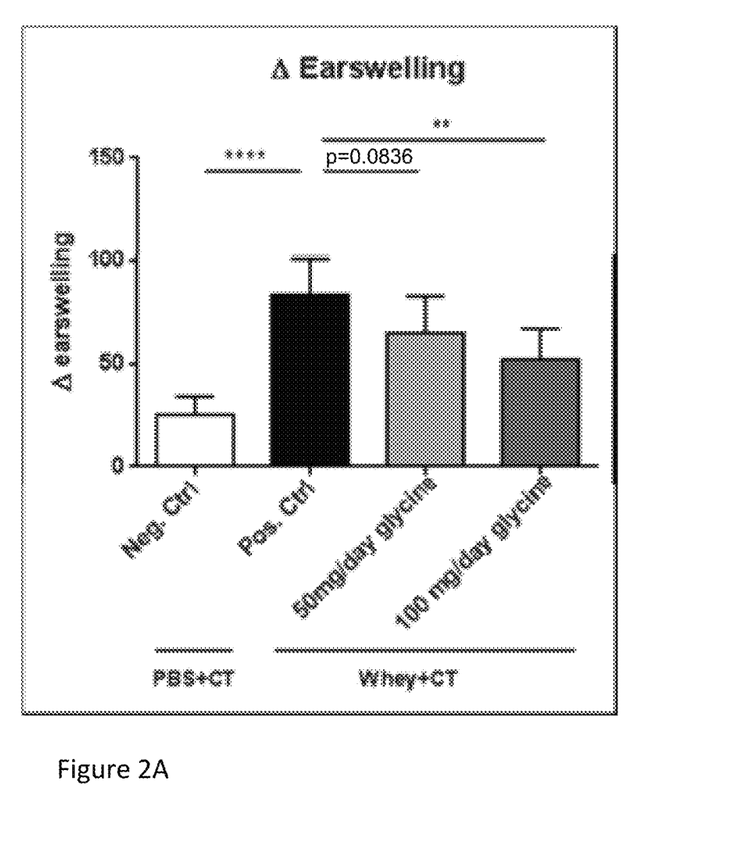
FIG. 2A depicts the results of glycine intake before sensitization inhibits the allergy development as indicated by the allergic skin response for ear-swelling after intradermal whey injection (FIG. 2A).
Figure 2B:
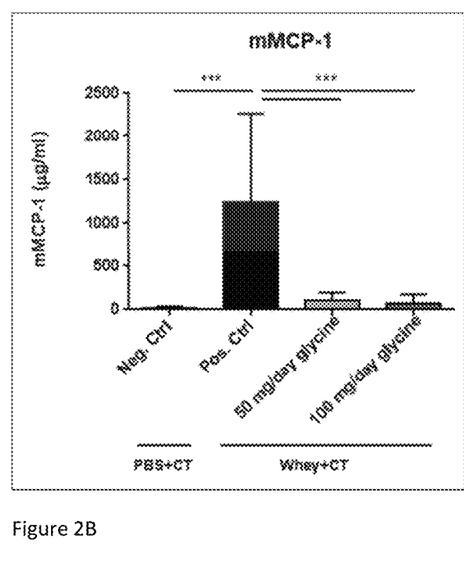
FIG. 2B depicts the results of glycine intake before sensitization inhibits the allergy as indicated by the mMCP1 release (by intestinal mast cells) after an oral allergen challenge.
Figure 2C:
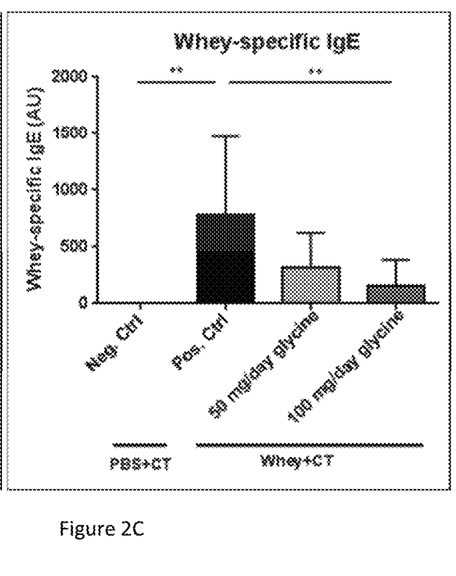
FIG. 2C depicts the results of glycine intake before sensitization inhibits the production of whey-specific IgE.

Results
Results are shown in FIGS. 2A-2C.

Glycine intake before sensitization inhibits the allergy development as indicated by the allergic skin response after intradermal whey injection. The effect was concentration dependent.

Glycine intake before sensitization inhibits allergy development as indicated by the mMCP1 release (by intestinal mast cells) after an oral allergen challenge.

Glycine intake before whey sensitization inhibits the production of whey-specific IgE.

Example 3: Glutamine Synergistically Enhances an Immunological Effect of Glycine The next experiment done by the inventor relates to the question whether amino acids are able to enhance immune effects of free glycine. To investigate this, human peripheral blood mononuclear cells (PBMCs) were stimulated with lipopolysaccharide (LPS) in the presence of free glycine in combination with different levels of free glutamine In short: Human PBMCs were obtained from buffy coats supplied by the blood bank and prepared by Ficoll gradient centrifugation according to standard methods. The recovered PBMCs were washed with PBS and cultured in RPMI-1640 containing, penicillin, streptomycin and 5% Fetal calf serum (FCS), 1.5E5 cells/well (96-wells culture plate). The cells were stimulated with LPS (*E. coli*, 055:B5, 10 ng/ml) for 20 hr after 1 hr pre-incubation with different levels of glycine in combination with different levels of glutamine. The tested levels of glycine and glutamine were also tested separately. TNF-α levels were detected in the supernatant of the cells using an ELISA kit.

Figure 3:
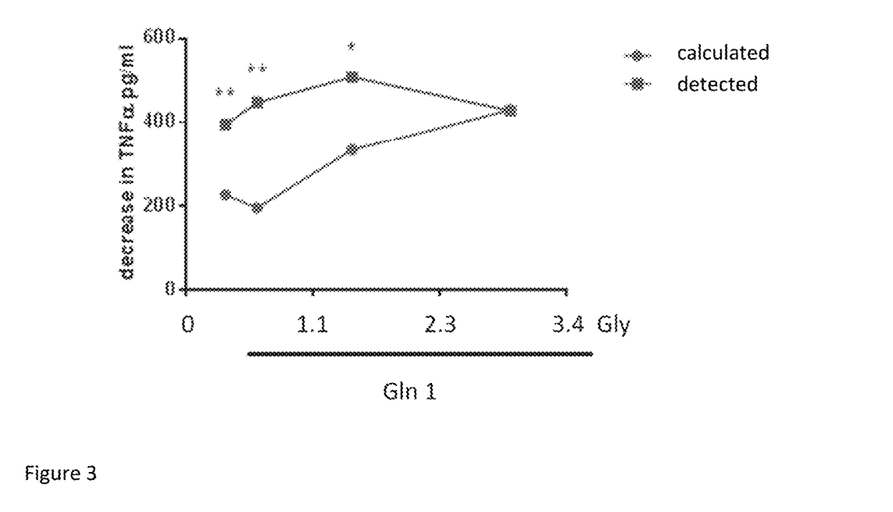
FIG. 3. Depicts the results that free glycine inhibited LPS induced TNF-α synthesis by PBMCs and that glutamine (at specific ratios) enhanced this effect synergistically.

Results are shown in FIG. 3. It was found that free glycine inhibited LPS induced TNF-α synthesis by PBMCs and that glutamine (at specific ratios) enhanced this effect synergistically. Depicted as calculated is the sum of the separate measured TNF-α decrease by glycine and glutamine when tested independently and as detected the effect as measured when the two amino acids were tested in combination at different ratios glycine/glutamine. At least at gly/gln ratios between 0.4 and 2.0 the TNF-alpha inhibiting effect was synergistic (statistically significant).

Without being bound by theory the inventors believe that this effect is also relevant for the induction of tolerance in the prevention of allergy, in that these two amino acids will also work synergistically in supporting immunologic tolerance induction itself.

The invention claimed is:

1. A method for inducing or improving tolerance against a food allergen in a human, comprising administering to the human a composition comprising at least one glycine source selected from the group consisting of an amino acid glycine, physiologically acceptable salts of the amino acid glycine, dipeptides having at least one glycine unit, tripeptides having at least one glycine unit and tetrapeptides having at least one glycine, the composition comprising at least 7 en % protein, wherein the protein is selected from the group consisting of hydrolysed protein, peptides, amino acids, salts of amino acids, and a combination thereof, and the total content of glycine provided by the glycine source is 60-350 mg/g total protein.

2. The method of claim 1, wherein the content of the glycine source is between 70 and 350 mg/g protein.

3. The method of claim 1, wherein the glycine source comprises at least one compound selected from the group consisting of the amino acid glycine and the physiologically acceptable salts of the amino acid glycine.

4. The method of claim 3, wherein the total content of the amino acid glycine or salt of the amino acid glycine is 60-350 mg/g protein.

5. The method of claim 1, wherein the food allergen is a milk protein and wherein the food allergy is a milk protein allergy.

6. The method of claim 1, wherein the composition is an infant formula comprising 7-12 en % protein, 35-65 en % carbohydrate and 30-60 en % fat.

7. The method of claim 6, wherein the composition further comprises a source of an amino acid glutamine, and the molar ratio glycine source:glutamine source of the composition is between 1:4 and 2:1.

8. The method of claim 1, wherein the composition comprises one or more prebiotics.

9. The method of claim 8, wherein the composition comprises at least one prebiotic selected from the group consisting of galactooligosaccharides (GOS) and fructooligosaccharides (FOS).

10. The method of claim 1, wherein the composition further comprises at least one long chain polyunsaturated fatty acid selected from the group consisting of alpha-linolenic acid (ALA), linoleic acid (LA), arachidonic acid (ARA), docosahexaenoic acid (DHA) and eicosapentaenoic acid (EPA).

11. The method of claim 1, wherein the composition is to be administered to provide a daily dosage per kg body weight of the human of 0.1-2 g glycine source.

12. The method of claim 11, wherein the daily dosage per kg body weight of glycine source is 0.1 1000 mg.

13. The method of claim 1, wherein said at least one glycine source induces or improves immunological tolerance against the food allergen.

14. A composition comprising protein, fat and carbohydrate, having at least 7 en % protein, wherein the protein is selected from the group consisting of hydrolysed protein, peptides, amino acids, salts of amino acids, and a combination thereof and at least 60 mg of a glycine source selected from the group consisting of an amino acid glycine, physiologically acceptable salts of the amino acid glycine, dipeptides having at least one glycine unit, tripeptides having at least one glycine unit and tetrapeptides having at least one glycine per gram protein and the protein consists of at least 80 wt % hydrolysed protein based on total weight of the protein in the composition.

15. A method for inducing or improving tolerance against an allergen in a human, comprising administering to the human, a composition comprising at least one glycine source selected from the group consisting of an amino acid glycine, physiologically acceptable salts of the amino acid glycine, dipeptides having at least one glycine unit, tripeptides having at least one glycine unit and tetrapeptides having at least one glycine unit, the composition comprising at least 7 en % protein, wherein the protein is selected from the group consisting of hydrolysed protein, peptides, amino acids, salts of amino acids, or a combination thereof, and the total content of glycine provided by the glycine source is 60-350 mg/g total protein.

16. The method of claim 15, wherein the human has a genetic predisposition to a food allergy, and/or at least one parent who has or has had a food allergy.

17. The method of claim 1, wherein the composition is a follow-on formula.

18. The method of claim 1, wherein the composition is a growing-up milk.

* * * * *